United States Patent [19]
Hofstetter et al.

[11] Patent Number: 5,975,077
[45] Date of Patent: Nov. 2, 1999

[54] METHOD AND APPARATUS FOR ASSISTING IN BREATHING

[75] Inventors: Andreas Hofstetter; Emil Arms, both of Bonaduz, Switzerland

[73] Assignee: Hamilton Medical, Inc., Reno, Nev.

[21] Appl. No.: 09/123,854

[22] Filed: Jul. 28, 1998

[51] Int. Cl.[6] .................................................. A61M 16/00
[52] U.S. Cl. ............................. 128/204.24; 128/204.25; 128/205.11; 128/207.18
[58] Field of Search .................. 128/204.24, 204.25, 128/205.11, 205.25, 206.11, 206.18, 207.13, 207.18

[56] References Cited

U.S. PATENT DOCUMENTS

| | | | |
|---|---|---|---|
| 2,831,487 | 4/1958 | Tafilaw | 128/207.18 |
| 3,913,607 | 10/1975 | Price | 128/205.11 |
| 4,151,843 | 5/1979 | Brekke et al. | 128/204.24 |
| 4,261,355 | 4/1981 | Glazener . | |
| 4,495,946 | 1/1985 | Lemer | 128/205.11 |
| 4,989,599 | 2/1991 | Carter | 128/207.18 |
| 5,193,532 | 3/1993 | Moa et al. . | |
| 5,243,971 | 9/1993 | Sullivan et al. | 128/207.18 |
| 5,273,032 | 12/1993 | Borody | 128/207.18 |
| 5,335,656 | 8/1994 | Bowe et al. | 128/204.11 |
| 5,560,354 | 10/1996 | Berthon-Jones et al. | 128/207.13 |

*Primary Examiner*—Aaron J. Lewis
*Attorney, Agent, or Firm*—Bernhard Kreten

[57] ABSTRACT

Apparatus for preventing lung collapse including an ambient air passageway, an airway injecting gas in fluid communication with nostrils of a patient and aerodynamically designed passageways for both the ambient air and the injected gas to optimize the fluid flow characteristics during inhalation and exhalation of the patient.

16 Claims, 8 Drawing Sheets

METHOD AND APPARATUS FOR ASSISTING IN BREATHING

FIELD OF THE INVENTION

The following invention relates generally to instrumentalities which assist in lung function. More specifically, the instant invention is directed to a method and apparatus which assists especially premature babies and others in utilization of their lungs, particularly when the patient is incapable of breathing without assistance.

BACKGROUND OF THE INVENTION

Babies born prematurely frequently lack the ability to keep their lungs from collapsing. Under normal circumstances, a baby's lungs will expand during inhalation and only partially contract during exhalation. Premature or newborn babies frequently have weak inspiratory movements causing collapse of the lung after exhalation. Collapse may also occur in the newborn as a result of blockage of bronchioles by mucus or from failure of the lung to distend.

For adults, lung collapse is a condition which may result from a lowering of intrapulmonic pressure or an increase in intrathoracic pressure. It may be focal, involving only a few lobules, or massive, in which an entire lobe or the complete lung is involved. It may result from obstruction of the bronchial tubes (obstructive atelectasis) or pressure upon the lung by air or fluid in the pleural cavity, an intrathoracic tumor, or a greatly enlarged heart (compressive atelectasis). Air may be introduced artificially into the pleural cavity (artificial pneumothorax) or it may be derived from emphysematous lesions.

The following patents reflect the state of the art of which applicant is aware and is included herewith to discharge applicant's acknowledged duty to disclose known prior art. It is stipulated, however, that neither patent teaches nor renders obvious when considered in any conceivable combination the nexus of the instant invention as disclosed in greater detail hereinafter and as particularly claimed.

| U.S. Pat. No. | ISSUE DATE | INVENTOR |
| --- | --- | --- |
| 4,261,355 | April 14, 1981 | Glazener |
| 5,193,532 | March 16, 1993 | Moa, et al. |

For example, the patent to Glazener teaches the use of a constant positive pressure breathing apparatus in which a cylindrical channel, serving as a conduit for gases either spontaneously or mechanically aspirated by a patient includes in said channel a narrow diameter nozzle venting compressed gas in the direction of inspired flow.

Moa, et al. teaches the use of a device for generating continuous positive airway pressure in which a fresh gas inlet channel admits gas into a breathing channel such that the fresh gas channel terminates substantially flush with the breathing channel.

SUMMARY OF THE INVENTION

The instant invention is distinguished over the known prior art in a multiplicity of ways. For example, an air passageway is provided having substantially uniform cross-section along its entire length and having a constant radius of curvature at an area upstream the site of admixture with a gas injector. The gas injector projects within the air passageway, having a body portion parallel to a cylindrical section of the passageway downstream from the curved area. Preferably, two injectors are provided sharing a common gas manifold. The injectors deliver gas via an outlet and under pressure at an area of the passageway where the passageway decreases to form (in cross-section) a constant radius end wall preferably having two portals. Each gas injector outlet is axially aligned with a respective portal both of which are preferably oriented to address the nostrils of the patient. Just upstream from the gas injector outlets, substantially laminar flow is exhibited, but at the site of gas injection, the gas and air combine and accelerate on the inhalation phase of the patient's breathing process by virtue of the decreasing, radiused end wall. Conversely, upon exhalation, flow beyond the portals (into the passageway) enters into a low pressure area with minimal back pressure and therefore results in a decrease in the velocity. However, at all times a residual gas pressure is provided by the injector which assures that the lungs of the patient will not collapse. Thus, a base line gas pressure always delivers adequate flow to prevent lung collapse. A flow monitoring passageway is provided to allow the device to communicate with flow monitoring equipment so that parameters may be modified as a function of patient breathing dynamics.

OBJECTS OF THE INVENTION

Accordingly, it is a primary object of the present invention to provide a new and novel method and apparatus for assisting patients, especially premature babies, in breathing.

A further object of the present invention is to provide a device as characterized above which is extremely safe to use and effective.

A further object of the present invention is to provide a device as characterized above which can be implemented on a patient with a modicum of skill.

A further object of the present invention is to provide a device as characterized above which lends itself to mass production techniques.

A further object of the present invention is to provide a device as characterized above which allows feed back from the respiratory process.

A further object of the present invention is to provide a device as characterized above which benefits from fluid flow dynamics within the apparatus.

A further object of the present invention is to provide a device as characterized above which is relatively comfortable even for a premature baby to wear.

Viewed from a first vantage point, it is an object of the present invention to provide a device to assist patients in breathing, comprising, in combination: first and second shells, the first shell being a mirror image of the second shell, the shells mated in registry about the mirror image to form a passageway, and a gas injector fixed within the passageway and having an outlet within the passageway and an inlet outside the passageway.

Viewed from a second vantage point, it is an object of the present invention to provide a method for providing constant gas flow pressure into a patient's lungs during inhalation and exhalation, the steps including: orienting an injector having pressurized gas adjacent an air inlet of the patient, and circumscribing the pressurized gas injector with an unpressurized passageway.

Viewed from a third vantage point, it is an object of the present invention to provide an inhalation assisting apparatus, comprising, in combination: a passageway having a portal, a gas injector projecting within the passageway and having a free end which proximately addresses the portal of the passageway, and means for attaching the apparatus to a patient's air breathing orifice adjacent the passageway's portal.

These and other objects will be made manifest when considering the following detailed specification when taken in conjunction with the appended drawing figures.

DESCRIPTION OF PREFERRED EMBODIMENTS

Figure 1:
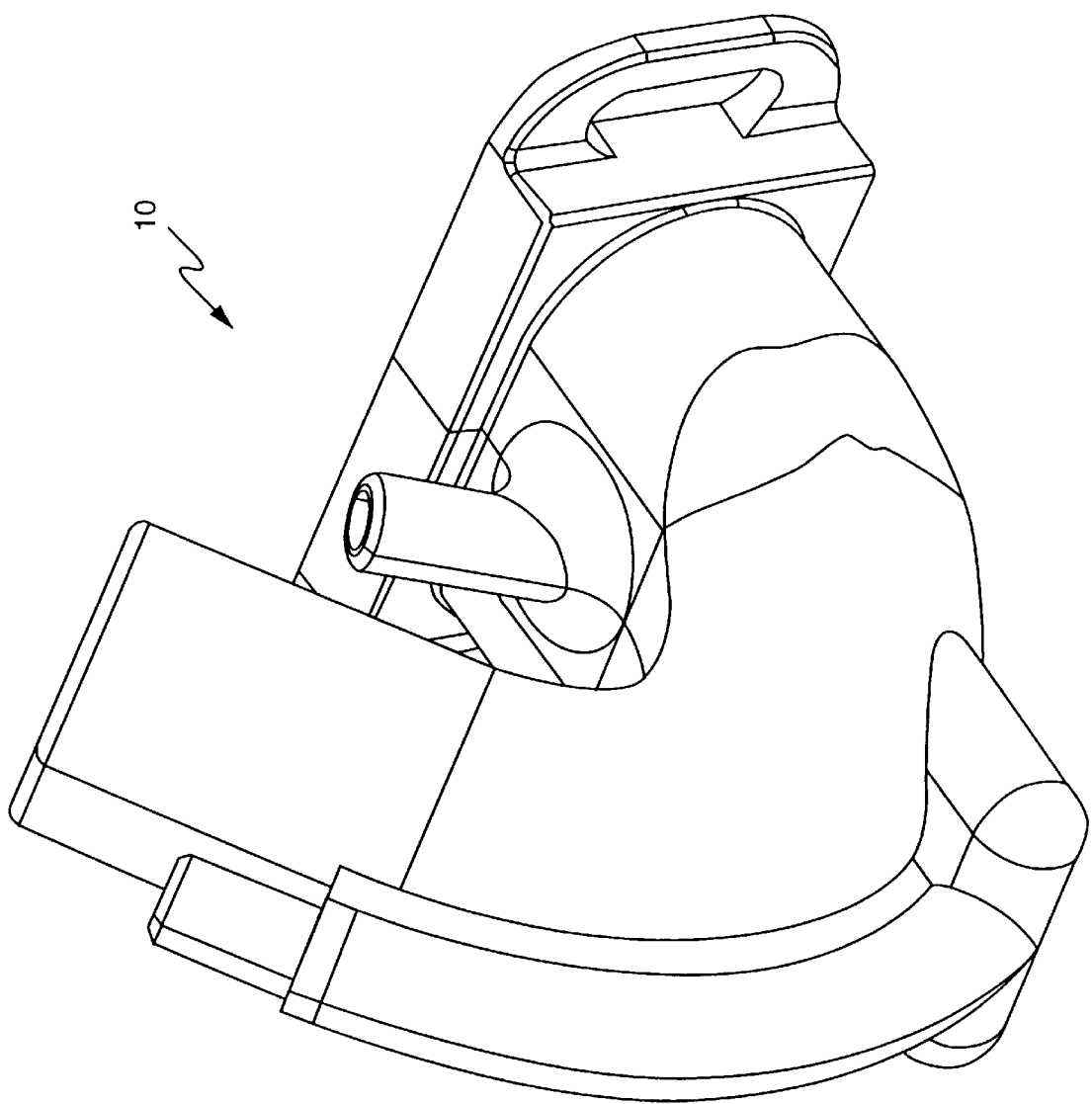
FIG. 1 is a perspective showing the apparatus according to the present invention.
Figure 2:
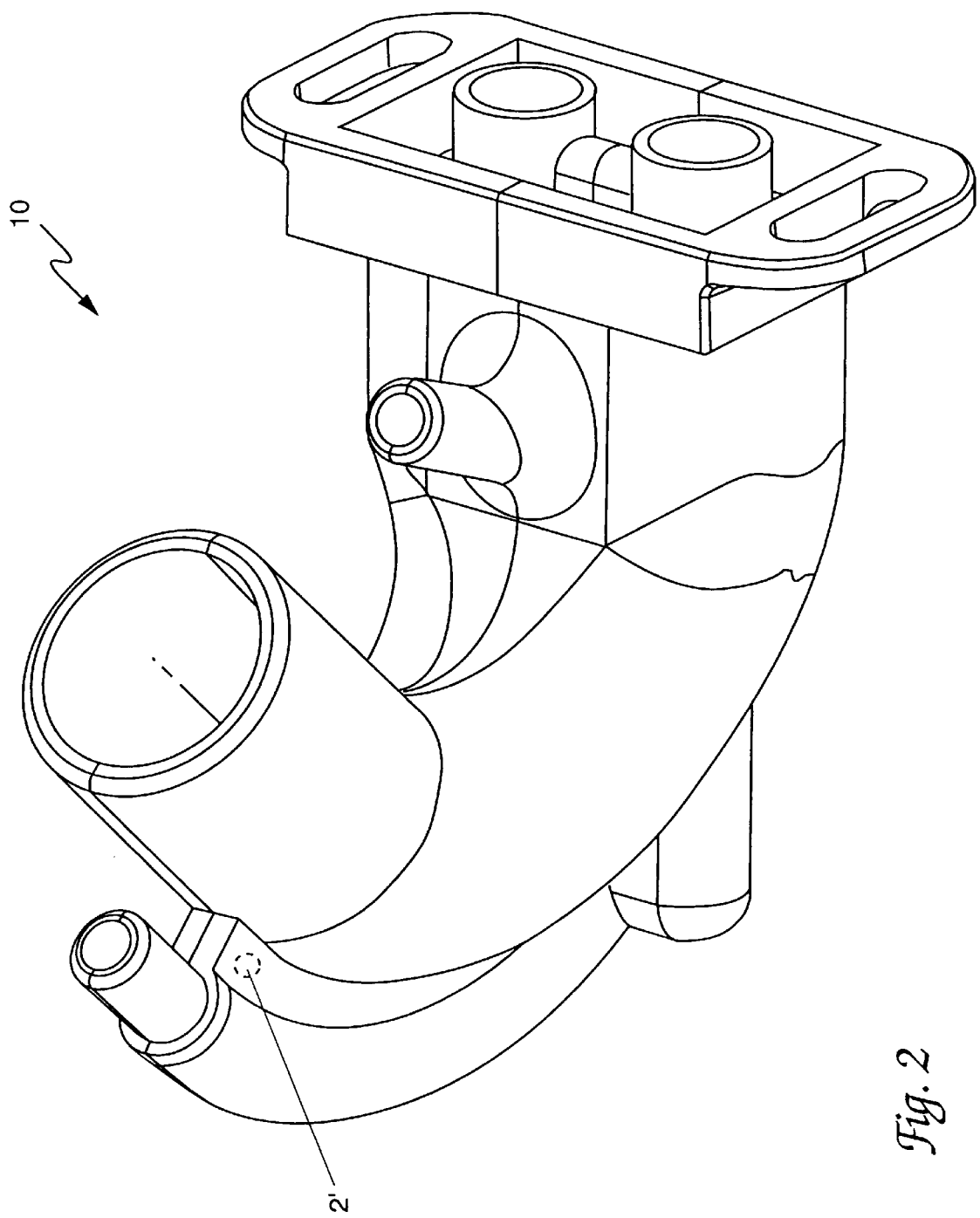
FIG. 2 is a perspective view from a different vantage point.
Figure 3:
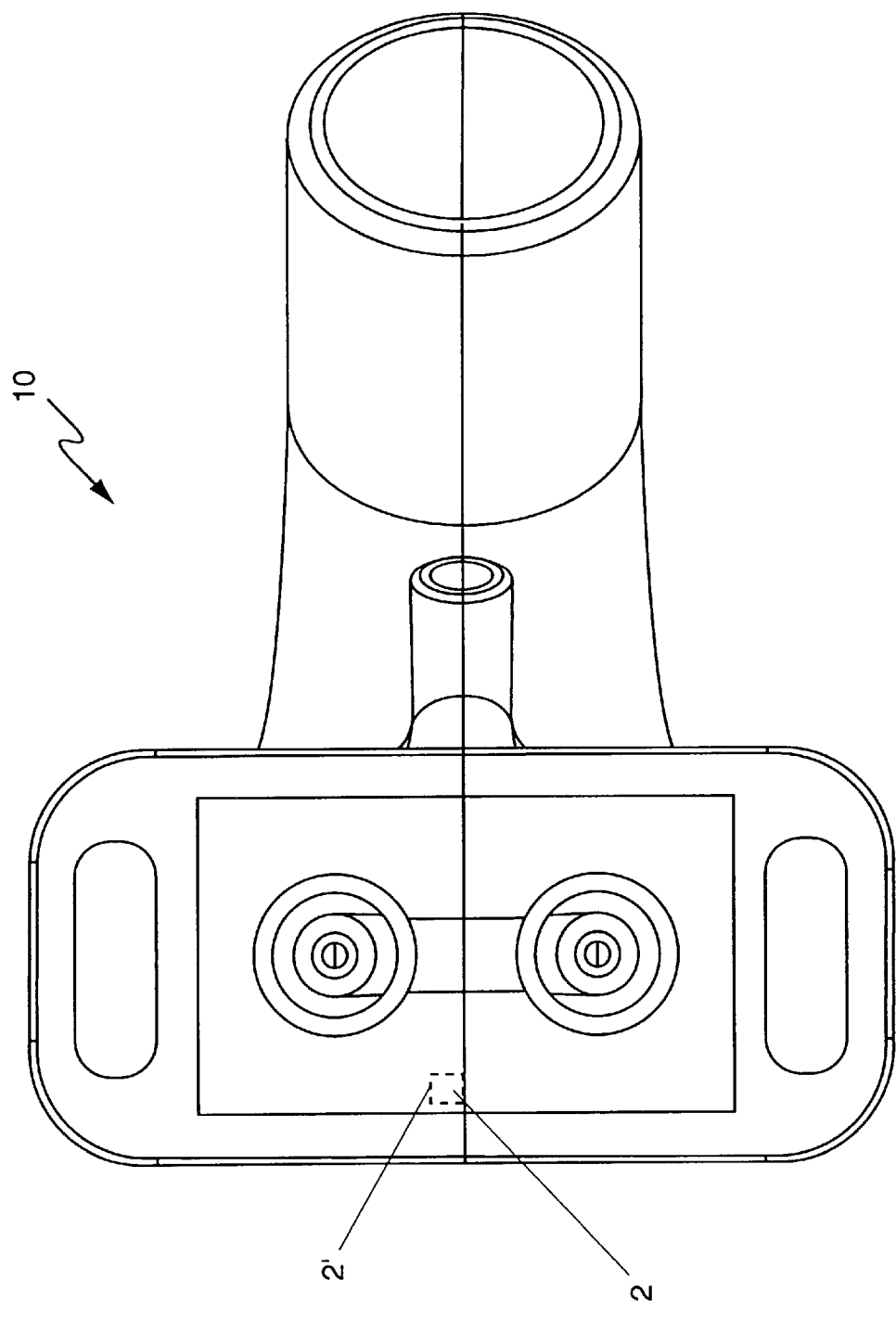
FIG. 3 is a plan view addressing the portals of the apparatus.
Figure 4:
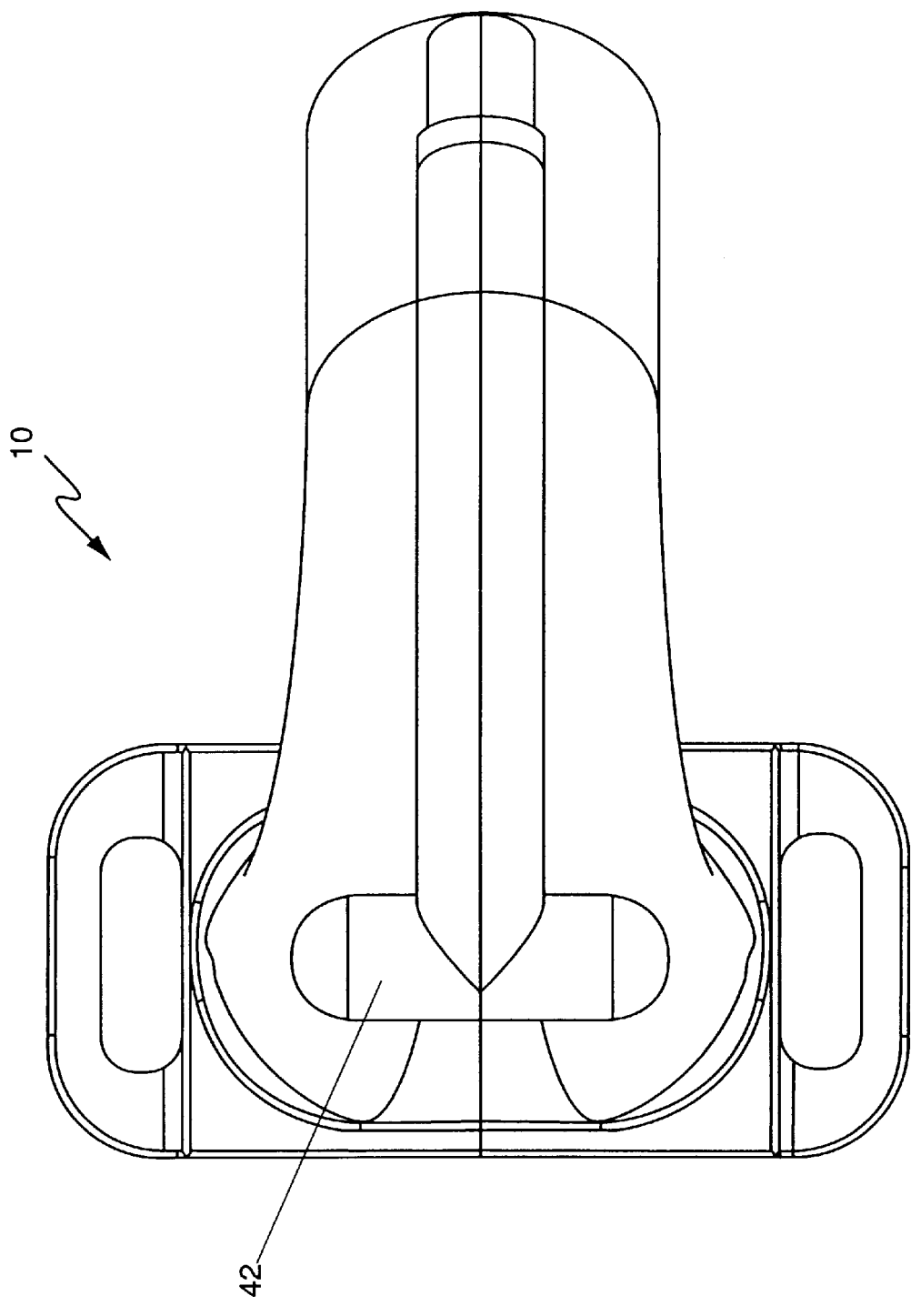
FIG. 4 is a top view opposite FIG. 3.

Considering the drawings, wherein like reference numerals denote like parts throughout the various drawing figures, reference numeral 10 is directed to the apparatus for assisting patients, especially premature babies, in breathing according to the present invention. Reference numeral 100 (FIGS. 8 and 9) is directed to the replaceable nostril piece to be used with apparatus 10.

Figure 5:
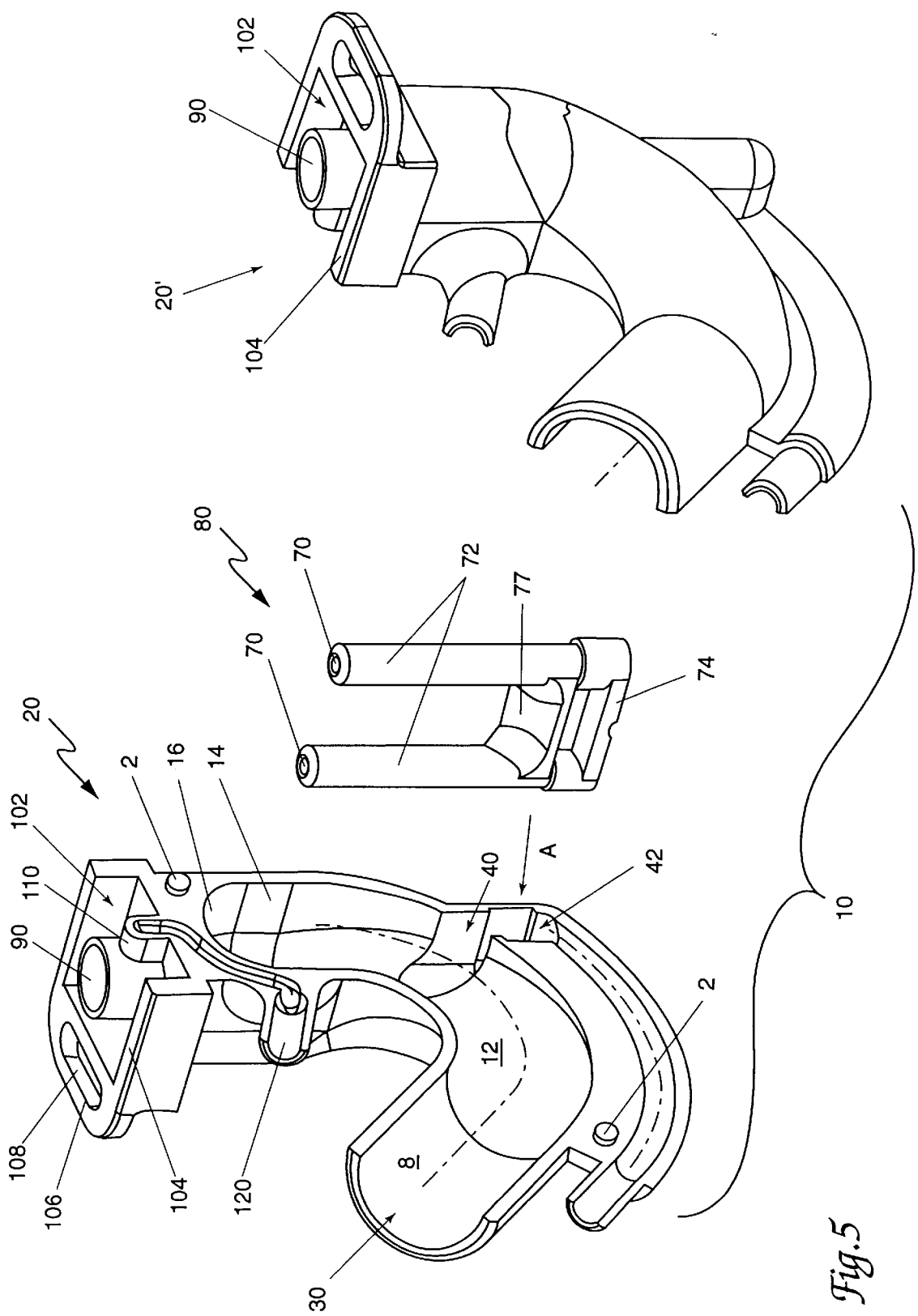
FIG. 5 is an exploded parts view in perspective of the apparatus.
Figure 9:
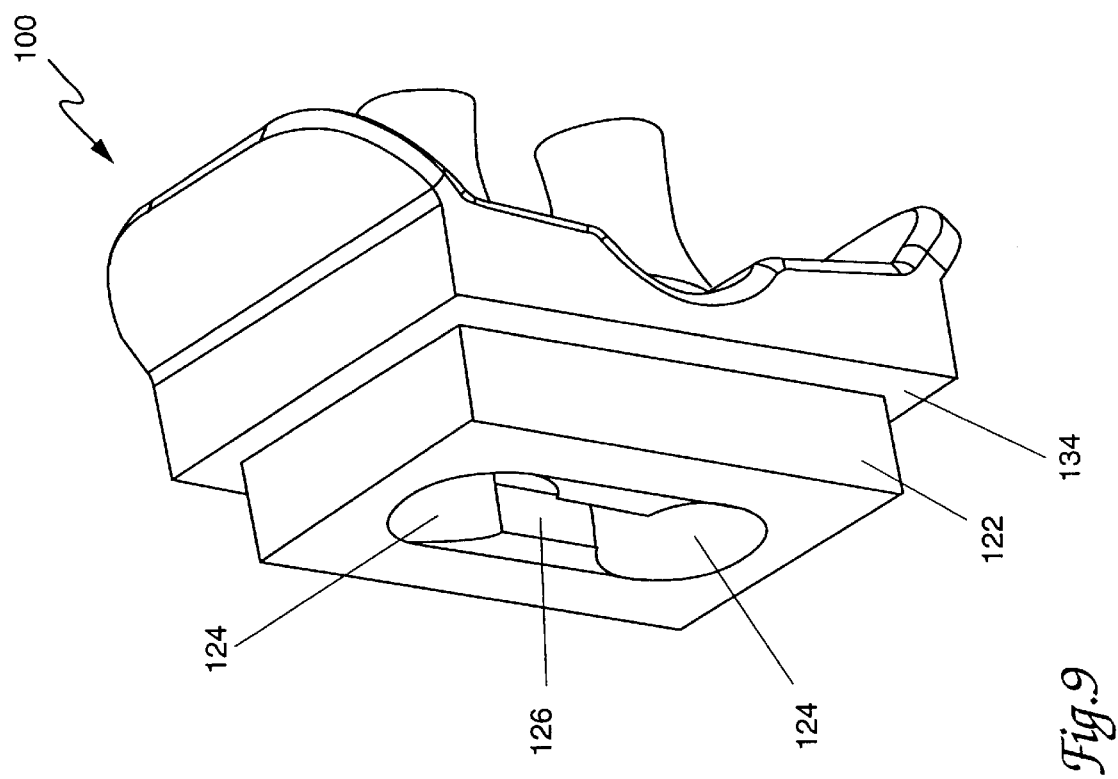
FIG. 9 is a perspective view from a different vantage point than that which is shown in FIG. 8.
Figure 8:
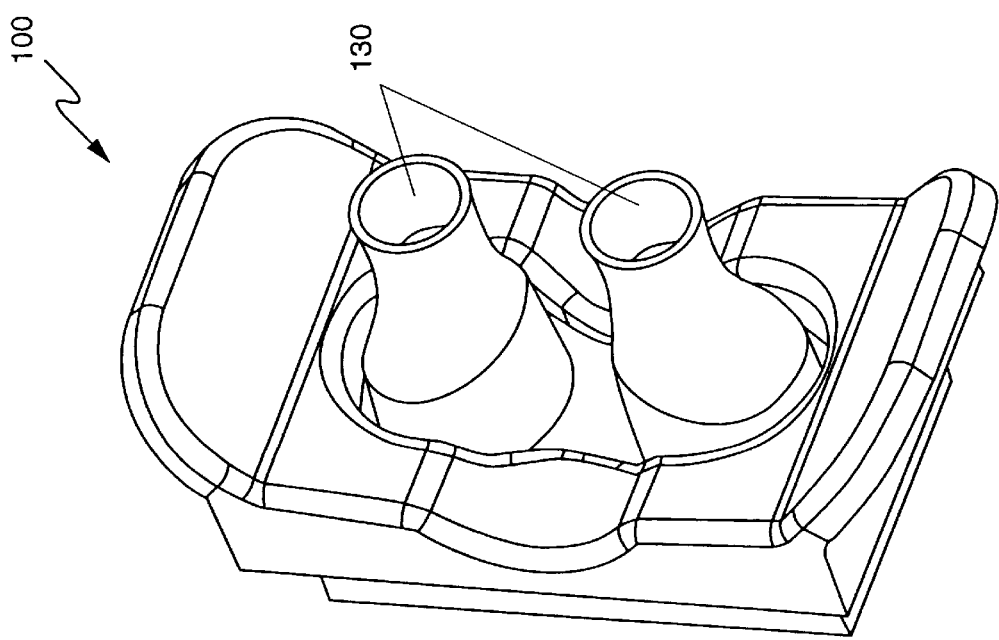
FIG. 8 is a perspective view of a removable nostril engaging element to be used with FIGS. 1 through 7.

In its essence, and referring to FIGS. 5, 8 and 9, the device includes two shells 20, 20', each being the mirror image of the other with the exception that the aligning pins 2 shown on the shell 20 mate within complementally formed recesses 2' on the other shell 20'. An injector 80 is removably attached to an interior of each of the shells so that, once inserted therewithin, each injector communicates with a portal 90 located adjacent an area where the nostril piece 100 frictionally fits. Collectively, the two shells 20, 20' combine to form a passageway 30 that allows unpressurized air to communicate with the portals 90. Pressurized gas passes through the injector 80 and beyond the portal 90 as will be explained.

Figure 6:
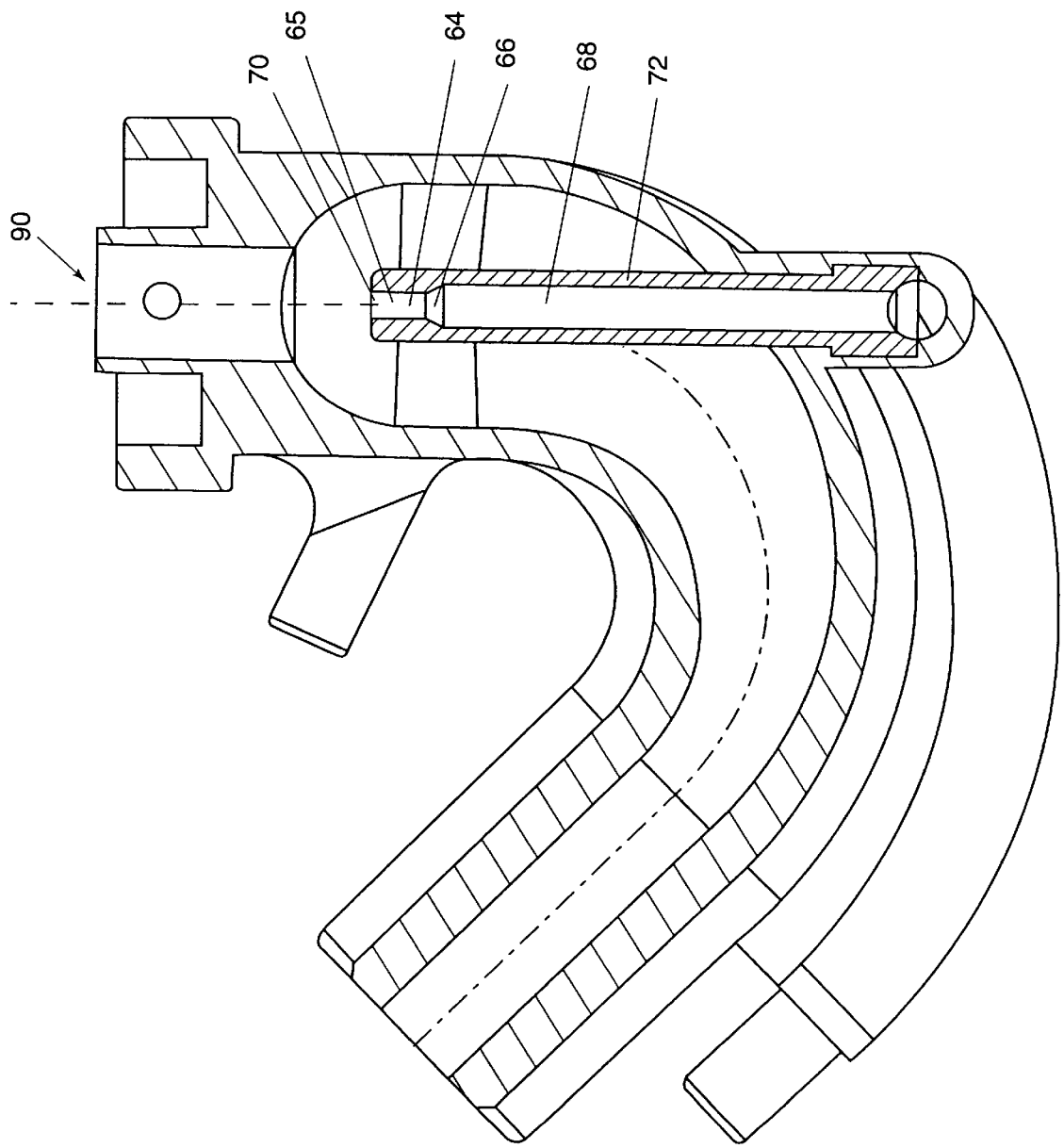
FIG. 6 is a sectional view of one of the shells and an associated injector.
Figure 7:
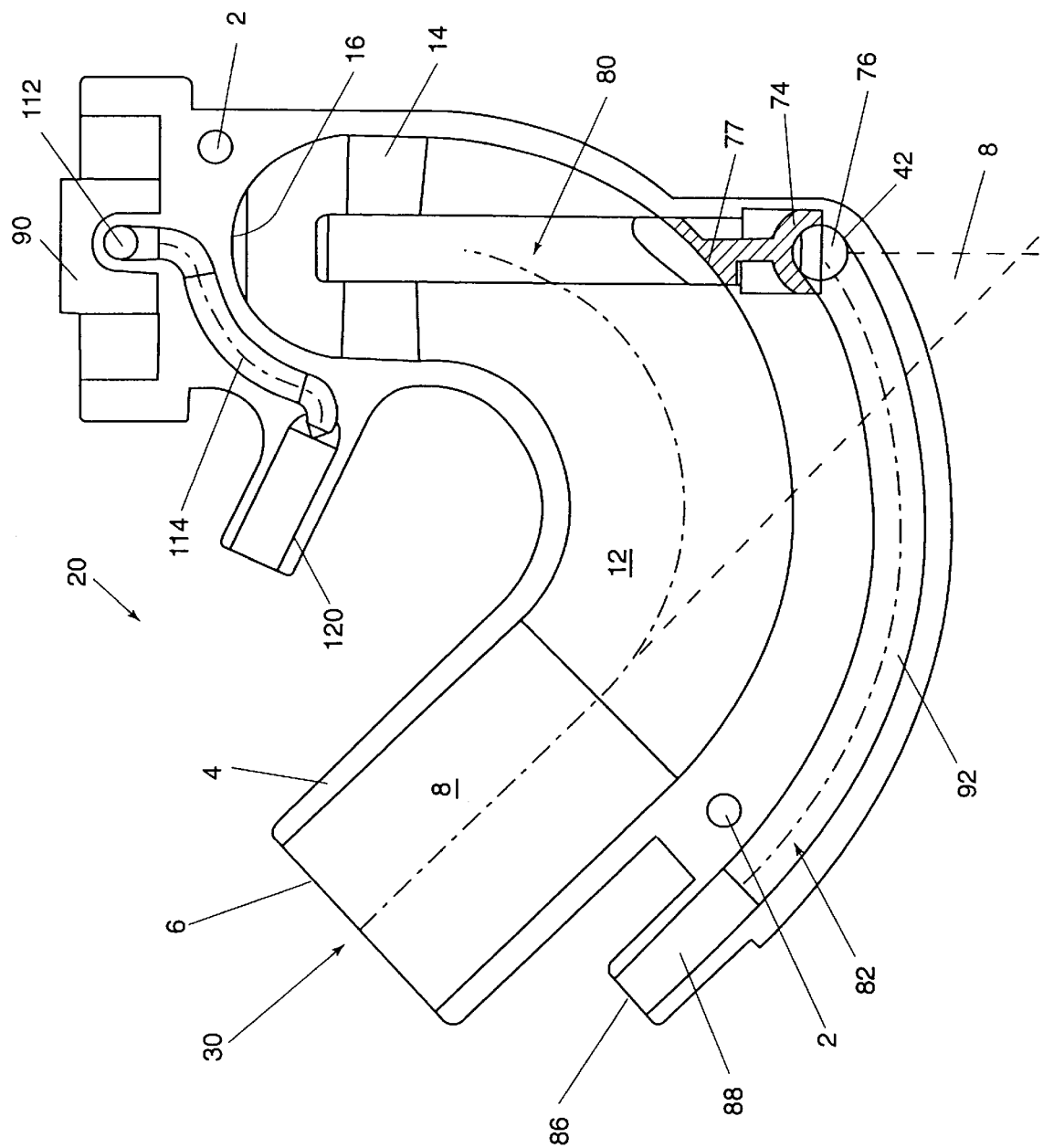
FIG. 7 is a side view of one of the shells and the injector, with part of the injector manifold shown in section.

More particularly, and with reference to FIG. 7, each shell 20, 20' is formed from plastic as by injection molding. The plastic has been molded to provide interior structure having the following geometric contour, with the provision that the shell have substantially uniform thickness so as to promulgate rapid part fabrication during injection molding. The passageway 30, surrounded and defined by the plastic 4 includes an inlet 6 of substantially circular contour defining an initial passageway 8 of substantially cylindrical dimension. A curved portion 12 redirects air flow about the curved passageway into a second linear, box-shaped passageway 14 slightly upstream from where the injector 80 allows gas to exit therefrom. The included angle subtended by the curved section 12 provides a relatively low profile when the device is mounted adjacent the nostrils of the patient providing clearance for other medical instrumentalities, such as an intubation device for the patient's mouth. In addition, the radiused section 12 provides a center of mass closer to the patient for greater stability. Preferably, the angle α subtended by the two linear passageways 8, 14 of the passageway 30 can vary between 30° and 60°, but is preferably 45°. It is preferred that through the radiused section 12, the cross-sectional area of the passageway diverges outwardly from cylindrical passageway 8 to the passageway 14 which is substantially rectangular in section. As shown in FIGS. 5 through 7, an end of the passageway 30 remote from the opening 6 and at an end of the passageway 14 terminates in an arcuate end wall 16, preferably of constant radius, interrupted only by the provision of a first and second portal 90 each axially aligned with an injector nozzle 70 of the injector 80. Each nozzle is offset from a geometrical center and in alignment with the two portals 90 which are oriented to substantially accommodate the spacing of a patient's nostrils.

The injector 80 holds the injector nozzles 70 in spaced apart relationship by means of first and second injector columns 72, each of substantially cylindrical configuration, and both having ends remote from nozzle 70 communicating with a flow manifold 74. The flow manifold 74 defines a top half of a cross-passageway 76 (FIG 7) to allow gas under pressure to be distributed equally to each of the columns 72 and out the injector nozzle 70. A bottom half of the cross-passageway is formed on a wall 42 of the recess 40. The cross-passageway 76 stops at each column 72. A support web 77 extends between the two columns 72 to provide rigidity. FIG. 6 reflects that the nozzle geometry includes a substantially cylindrical interior portion 68 having a stepped-down portion 66 of substantially truncated, conical configuration terminating adjacent the nozzle 70 defined by a necked-down and smaller diameter cylindrical section 64. Cross-passageway 76 is about the same diameter as airway 82 (FIG 7).

The injector 80 is slideably disposed within a recess 40 complementally formed in each of the shells 20, 20'. In assembly, the injector 80 (FIG. 5) is moved in the direction of the arrow "A" for one half of a shell, and then the other half of the shell is placed thereover properly oriented by means of the alignment pins 2 and their associated recesses 2'. The injector 80 receives gas under pressure from an injector airway 82 (FIG. 7) formed in each half of the shell. The airway 82 parallels the linear and curved sections of the passageway 30. It includes an opening 86 of substantially circular configuration followed by a constant cross-section linear section 88, thence to a constant radius of curvature medial portion 92 terminating in the cross tube 76. The medial portion 92 is preferably of constant cross-section, equal to the linear section 88. As mentioned, each injector column 72 communicates with the cross tube 76 and projects beyond the linear portion 14 of the passageway 30 terminating within the domed arcuate end wall 16 of the passageway 30 near the portal 90. The cylindrical portion 64 of the injector has a central point 65 (FIG 6) which approximately coincides with the radius of curvature of the domed portion. Preferably, the diameter of the passageway 30 is four times greater than the diameter of the airway 82. Preferably, the cross-sectional area of each cylindrical injector portion 68 is one-half the circular cross-section in the airway 82. Preferably, the nozzle cross-sectional diameter 64 is one-fourth that of the circular cross-section of the airway 82. This assures good flow pressure.

Referring to FIGS. 8 and 9, perspective views of the removable nostril piece 100 can be explored in respect of its relationship to the portals 90. The nostril piece 100 frictionally fits within a well 102 formed in each half of the shell 20, 20'. Collectively, the well 102 defines an open top box from which the portal 90 projects. It is preferred that the portals 90 extend above an uppermost dimension of the well, the well having a peripheral wall 104 oriented in plane. Lateral extremities of the peripheral wall transition into ears 106, each having openings 108 to allow a strap to be threaded therethrough so as to provide a means of attaching the apparatus around the head of the patient. Each portal 90 also includes a duct 110 projecting from a side wall of the cylindrical portal 90, the duct 110 allowing at least a modicum of air to pass through an opening 112 extending between the portal 90 and the duct 110 and thence to a passageway 114 in communication with a flow monitoring pipe 120.

The well 102 frictionally receives within side walls thereof a block member 122 having an exterior dimension complemental to the dimension of the well 102 to frictionally and tightly, sealingly receive therein the nostril piece 100. Block 122 on a bottom face thereof includes openings 124 to frictionally override the outer periphery of the portals 90 in tight, sealing engagement. A relief 126 extends between the openings 124 and serves as a saddle to ride atop duct 110.

A side of the nostril piece 100 opposite the box 122 includes a pair of nostril engaging flexible stems 130 hollow and in fluid communication with the openings 124 and therefore the portals 90. Peripheral wall 104 of the well 102 receives a ledge 134 of the nostril piece 100 to ensure no air leakage.

In use and operation, flow characteristics at the portal 90 can be monitored via the pipe 120 at its outlet. On the inspiration phase, ambient air 30 moves inward along the passageway. Upon exhalation it moves outward, but at all times, a constant source of pressure is provided through the injector 80. Thus, a base pressure is always administered to the patient to prevent the lungs from collapsing. In addition, the relationship between the cross-sectional areas of the passageway 30, the airway 82, the injector outlet 64 and the injector tube 68 assure that the pressure delivered by the injector is properly delivered. The domed arcuate end wall 16 further provides fluid flow inhalation acceleration and a low pressure area on exhalation as explained hereinabove.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A device to assist a patient in breathing, comprising, in combination:
    first and second shells, said first shell being a mirror image of said second shell, said shells mated in registry about said mirror image to form a passageway, and
    a gas injector fixed within said passageway and having an outlet within said passageway and an inlet outside said passageway.
2. The device of claim 1 wherein said gas injector includes means for accelerating fluid flow therethrough.
3. The device of claim 2 wherein said fluid flow acceleration means includes a converging nozzle adjacent a portal communicating with nostrils of the patient.
4. The device of claim 3 including a nostril piece removeably attached to said device whereby the nostril piece can be replaced.
5. The device of claim 4 including a fluid flow monitoring outlet integrally formed with said shells and in fluid communication with said portal.
6. The device of claim 5 further including said passageway having an initial section of substantially constant circular cross-section, a medial section having a constant radius of curvature and diverging outwardly away from said first section and a substantially rectangular chamber connected to said outwardly diverging end, an airway in fluid communication with said gas injection including a manifold for dividing airway fluid flow into two injector nozzles oriented in spaced relation in registry with a pair of said portals for injection into the nostrils of the patient.
7. A method for providing constant gas flow pressure into a patient's lungs during inhalation and exhalation, the steps including:
    orienting an injector having pressurized gas adjacent an air inlet of the patient,
    circumscribing the pressurized gas injector with an unpressurized passageway, and monitoring fluid flow adjacent the air inlet of the patient.
8. The method of claim 7 including providing a converging area in the injector, accelerating gas flow.
9. An inhalation assisting apparatus, comprising, in combination:
    a passageway having a portal,
    a gas injector projecting within said passageway and having a free end which proximately addresses said portal of said passageway,
    means for attaching said apparatus to a patient's air breathing orifice adjacent said passageway's portal, and
    means for monitoring fluid flow adjacent said passageway's portal.
10. The apparatus of claim 9 wherein said fluid flow monitoring means includes a passageway extending from an opening located on a sidewall of said portal to a flow monitoring pipe.
11. The apparatus of claim 9 wherein said apparatus is formed from first and second shells, said shells being mirror images of each other and mated to form said passageway, said shells including alignment pins and complemental recesses to facilitate assembly.
12. A method for providing constant gas flow pressure into a patient's lungs during inhalation and exhalation, the steps including:
    orienting an injector having pressurized gas adjacent an air inlet of the patient, and
    circumscribing the pressurized gas injector with an unpressurized passageway,
    providing a converging area in the injector, accelerating gas flow, and
    monitoring fluid flow adjacent an air inlet of the patient.
13. The method of claim 12 including forming a shell around the injector from two pieces of plastic.
14. The method of claim 13 including attaching a nostril piece to the patient and the shell.
15. The method of claim 14 including decelerating exhaust gas from the patient.
16. The method of claim 15 including providing one injector per nostril.

* * * * *